(12) United States Patent
Lookadoo et al.

(10) Patent No.: US 11,982,680 B2
(45) Date of Patent: May 14, 2024

(54) DEVICES, SYSTEMS, AND METHODS FOR MEASURING BIOMARKERS IN BIOLOGICAL FLUIDS

(71) Applicant: Jana Care, Inc., Boston, MA (US)

(72) Inventors: Daniel B. Lookadoo, Boston, MA (US); Ashok A. Kumar, Malden, MA (US); Jeremy E. Schonhorn, Hopkinton, MA (US); Christopher M. Uherek, Boston, MA (US); Michal Depa, Beaconsfield (CA)

(73) Assignee: Jana Care, Inc., Watertown, MA (US)

( * ) Notice: Subject to any disclaimer, the term of this patent is extended or adjusted under 35 U.S.C. 154(b) by 0 days.

(21) Appl. No.: 18/078,688

(22) Filed: Dec. 9, 2022

(65) Prior Publication Data
US 2023/0176079 A1 Jun. 8, 2023

Related U.S. Application Data

(63) Continuation of application No. 16/818,976, filed on Mar. 13, 2020, now Pat. No. 11,536,732.

(51) Int. Cl.
*G01N 33/70* (2006.01)
*G01N 33/535* (2006.01)
(Continued)

(52) U.S. Cl.
CPC ........... *G01N 33/70* (2013.01); *G01N 33/535* (2013.01); *G01N 33/6893* (2013.01);
(Continued)

(58) Field of Classification Search
CPC .. G01N 33/70; G01N 33/535; G01N 33/6893; G01N 35/00069; G01N 33/54388; G16C 20/10; H04W 84/18; C12Q 1/50
See application file for complete search history.

(56) References Cited

U.S. PATENT DOCUMENTS

| 4,772,561 A | 9/1988 | Genshaw |
| 4,816,224 A | 3/1989 | Vogel et al. |

(Continued)

FOREIGN PATENT DOCUMENTS

| BR | 112018014560 A2 | 12/2018 |
| CN | 1672631 A | 9/2005 |

(Continued)

OTHER PUBLICATIONS

Aviad, "Dario—Turning Your Smartphone into a Glucose Meter," Dec. 5, 2012, 4 pages.

(Continued)

*Primary Examiner* — Jill A Warden
*Assistant Examiner* — Michael Paul Shimek
(74) *Attorney, Agent, or Firm* — Husch Blackwell LLP (57) ABSTRACT

Platforms for enzymatic assays for biomarkers, including systems, methods, and measuring devices by which a biomarker, such as creatinine, is measured using a small amount of biological fluid, such as blood, plasma, or serum. The measuring device or biosensor can be a test strip including a layered active component assembly positioned between two outer layers which enables multi-step enzymatic reactions operating in kinetic and/or endpoint (in which the reaction is allowed to near completion), and generally includes multiple layers with primary enzyme(s), coupling enzyme(s), and reagents to produce an optical signal correlated to the concentration of a biomarker in the sample. The test strip can be read using a portable optical reader coupled to a smart phone or tablet.

19 Claims, 5 Drawing Sheets

(51) Int. Cl.
  *G01N 33/68* (2006.01)
  *G01N 35/00* (2006.01)
  *G16C 20/10* (2019.01)
  *H04W 84/18* (2009.01)
(52) U.S. Cl.
  CPC ....... *G01N 35/00069* (2013.01); *G16C 20/10* (2019.02); *H04W 84/18* (2013.01)

(56) References Cited

U.S. PATENT DOCUMENTS

| | | |
|---|---|---|
| 5,112,124 A | 5/1992 | Harjunmaa et al. |
| 5,186,843 A | 2/1993 | Baumgardner et al. |
| 5,304,468 A | 4/1994 | Phillips et al. |
| 5,372,135 A | 12/1994 | Mendelson et al. |
| 5,379,214 A | 1/1995 | Arbuckle |
| 5,506,144 A | 4/1996 | Sundrehagen |
| 5,597,532 A | 1/1997 | Connolly |
| 5,622,868 A | 4/1997 | Clarke et al. |
| 5,631,364 A | 5/1997 | Sundrehagen et al. |
| 5,702,952 A | 12/1997 | Sundrehagen et al. |
| 5,919,708 A | 7/1999 | Sundrehagen |
| 6,024,919 A | 2/2000 | Nelson et al. |
| 6,106,732 A | 8/2000 | Johnston et al. |
| 6,295,506 B1 | 9/2001 | Heinonen et al. |
| 6,491,870 B2 | 12/2002 | Patel et al. |
| 6,509,196 B1 | 1/2003 | Brooks et al. |
| 6,574,425 B1 | 6/2003 | Weiss et al. |
| 6,628,829 B1 | 9/2003 | Chasen |
| 7,041,468 B2 | 5/2006 | Drucker et al. |
| 7,045,361 B2 | 5/2006 | Heiss et al. |
| 7,414,758 B2 | 8/2008 | Vaughn |
| 7,507,550 B2 | 3/2009 | Spinke et al. |
| 7,514,039 B2 | 4/2009 | Loomis et al. |
| 7,809,418 B2 | 10/2010 | Xu |
| 7,830,519 B2 | 11/2010 | Mah et al. |
| 7,935,307 B2 | 5/2011 | Angelides |
| 8,009,884 B2 | 8/2011 | Chio |
| 8,145,431 B2 | 3/2012 | Kloepfer et al. |
| 8,158,080 B2 | 4/2012 | Bae et al. |
| 8,172,994 B2 | 5/2012 | Lee |
| 8,204,566 B2 | 6/2012 | Schurman et al. |
| 8,372,630 B2 | 2/2013 | Uematsu et al. |
| 8,391,945 B2 | 3/2013 | Say et al. |
| 8,394,328 B2 | 3/2013 | Neel et al. |
| 8,467,843 B2 | 6/2013 | Markle et al. |
| 8,597,188 B2 | 12/2013 | Bernstein et al. |
| 8,700,115 B2 | 4/2014 | Markle et al. |
| 8,935,007 B2 | 1/2015 | Kloepfer et al. |
| 9,241,663 B2 | 1/2016 | Jena et al. |
| 9,383,352 B2 | 7/2016 | Nagalla et al. |
| 10,436,773 B2 | 10/2019 | Depa et al. |
| 11,231,411 B2 | 1/2022 | Depa et al. |
| 11,536,732 B2 * | 12/2022 | Lookadoo ........ G01N 35/00069 |
| 2002/0146345 A1 | 10/2002 | Neilson et al. |
| 2003/0009088 A1 | 1/2003 | Korth et al. |
| 2003/0050537 A1 | 3/2003 | Wessel |
| 2003/0073243 A1 | 4/2003 | Law et al. |
| 2003/0113227 A1 | 6/2003 | Eyster et al. |
| 2003/0175806 A1 | 9/2003 | Rule et al. |
| 2005/0095697 A1 | 5/2005 | Bachur, Jr. et al. |
| 2005/0227370 A1 | 10/2005 | Ramel et al. |
| 2006/0222567 A1 | 10/2006 | Kloepfer et al. |
| 2006/0240541 A1 | 10/2006 | Petruno et al. |
| 2006/0292039 A1 | 12/2006 | Ilida |
| 2007/0081920 A1 | 4/2007 | Murphy et al. |
| 2007/0177032 A1 | 8/2007 | Wong |
| 2008/0008370 A1 | 1/2008 | Chio |
| 2008/0025599 A1 | 1/2008 | Cho et al. |
| 2008/0166791 A1 | 7/2008 | Kim et al. |
| 2009/0093012 A1 | 1/2009 | Minami |
| 2009/0163415 A1 | 6/2009 | Katrukha et al. |
| 2009/0227855 A1 | 9/2009 | Hill et al. |
| 2010/0044441 A1 | 2/2010 | Cohen et al. |
| 2010/0110439 A1 | 5/2010 | Gruler et al. |
| 2010/0145733 A1 | 6/2010 | Drucker et al. |
| 2010/0222648 A1 | 9/2010 | Siekmann |
| 2010/0254581 A1 | 10/2010 | Nesser et al. |
| 2010/0312483 A1 | 12/2010 | Peyser et al. |
| 2010/0317951 A1 | 12/2010 | Rutkowski et al. |
| 2011/0019883 A1 | 1/2011 | Bremnes et al. |
| 2011/0038765 A1 | 2/2011 | Drucker et al. |
| 2011/0261355 A1 | 10/2011 | Hannel et al. |
| 2011/0275162 A1 | 11/2011 | Tong et al. |
| 2011/0308313 A1 | 12/2011 | Azimi et al. |
| 2012/0082374 A1 | 4/2012 | Agarwal et al. |
| 2012/0142084 A1 | 6/2012 | Dunne et al. |
| 2012/0189509 A1 | 7/2012 | Hsiao |
| 2012/0302456 A1 | 11/2012 | Whitesides et al. |
| 2013/0083820 A1 | 4/2013 | Barwell et al. |
| 2013/0273528 A1 | 10/2013 | Ehrenkranz |
| 2013/0276521 A1 | 10/2013 | Fuerst et al. |
| 2014/0072189 A1 * | 3/2014 | Jena ............... G01N 21/8483 |
| | | 382/128 |
| 2014/0099237 A1 | 4/2014 | Tung et al. |
| 2014/0170757 A1 | 6/2014 | Tsai et al. |
| 2014/0236489 A1 | 8/2014 | Chen |
| 2014/0271362 A1 | 9/2014 | Markovsky et al. |
| 2015/0160203 A1 | 6/2015 | Choi et al. |
| 2015/0226736 A1 | 8/2015 | Nguyen et al. |
| 2015/0335272 A1 | 11/2015 | Natale et al. |
| 2015/0359458 A1 | 12/2015 | Erickson et al. |
| 2017/0234858 A1 | 8/2017 | Depa et al. |
| 2018/0011105 A1 | 1/2018 | Nakamura et al. |
| 2019/0187154 A1 | 6/2019 | Kumar et al. |
| 2019/0232287 A1 | 8/2019 | Depa et al. |
| 2020/0096501 A1 | 3/2020 | Depa et al. |
| 2021/0285972 A1 | 9/2021 | Lookadoo et al. |

FOREIGN PATENT DOCUMENTS

| | | |
|---|---|---|
| CN | 102509064 A | 1/2008 |
| CN | 101545864 A | 9/2009 |
| CN | 101688840 A | 3/2010 |
| CN | 101999881 A | 4/2011 |
| CN | 102023158 A | 4/2011 |
| CN | 104812292 A | 7/2015 |
| CN | 206920451 U | 1/2018 |
| CN | 108712877 A | 10/2018 |
| CN | 109916895 A | 6/2019 |
| EP | 1710565 A1 | 10/2006 |
| EP | 2104847 A4 | 1/2013 |
| EP | 2893477 A2 | 7/2015 |
| EP | 3405100 A4 | 10/2019 |
| EP | 3561511 A1 | 10/2019 |
| EP | 3724659 A1 | 10/2020 |
| JP | 2007-523335 A | 8/2007 |
| JP | 2007-538230 A | 12/2007 |
| JP | 2008-286522 A | 11/2008 |
| JP | 2010-190867 A | 9/2010 |
| JP | 2014-185958 A | 10/2014 |
| JP | 2015-533211 A | 11/2015 |
| JP | 2016-509206 A | 3/2016 |
| JP | 6326574 B2 | 5/2018 |
| JP | 2019-510203 A | 4/2019 |
| KR | 10-2013-0066841 A | 6/2013 |
| KR | 1011454215 B1 | 10/2014 |
| WO | WO 1990/002950 A1 | 3/1990 |
| WO | WO 1999/022236 A1 | 5/1999 |
| WO | WO 2002/090995 A2 | 11/2002 |
| WO | WO 2008/086246 A1 | 7/2008 |
| WO | WO 2010/142447 A1 | 12/2010 |
| WO | WO 2011/023760 A1 | 3/2011 |
| WO | WO 2012/060810 A1 | 5/2012 |
| WO | WO 2013/028784 A1 | 2/2013 |
| WO | WO 2013/117233 A1 | 8/2013 |
| WO | WO 2014/037820 A2 | 3/2014 |
| WO | WO 2017/127349 A1 | 7/2017 |

(56) References Cited

FOREIGN PATENT DOCUMENTS

| | | |
|---|---|---|
| WO | WO 2019/118971 A1 | 6/2019 |
| WO | WO 2019/152508 A1 | 8/2019 |

OTHER PUBLICATIONS

Ballard, "Generalizing the Hough Transform to Detect Arbitrary Shapes," vol. 13, No. 2, p. 111-122, Oct. 10, 1979, 12 pages.
Canny, "A Computational Approach to Edge Detection," IEEE Trans. Pattern Analysis and Machine Intelligence, 8(6), pp. 679-698, 1986.
Cass, "Modified iPhone Can Detect Blood Disorders," Technology Review, Oct. 5, 2011, 2 pages.
Darma, "iPhone Transformed into Microscope and Spectrometer," Medgadget, Oct. 4, 2011, 3 pages.
Dell, et al., "Towards a Point-of-Care Diagnostic System: Automated Analysis of Immunoassay Test Data on a Cell Phone," NSDR, Jun. 28, 2011, 6 pages.
Dolan, "Misfit Wearables launches Shine, an elegant but rugged activity tracker," mobihealthnews, Nov. 14, 2012, 5 pages.
Duda, et al., "Use of the Hough Transformation to Detect Lines and Curves in Pictures," Communications of the ACM, vol. 15, Jan. 1972, 5 pages.
Džimbeg-malčić, V., Barbarić-mikoević, Ž. & Itrić, K. Kubelka-Munk Theory in Describing Optical Properties of Paper ( I ); 1, 117-124 (2011) (Kubelka Munk theory), 8 pages.
EIN Presswire, "Philosys, Inc. Receives FDA Approval for Gmate Voice Blood Glucose Meter," Mar. 18, 2013, 2 pages.
Frantzen, F. et al. Glycohemoglobin filter assay for doctors' offices based on boronic acid affinity principle. Clin. Chem. 43, 2390-2396 (1997) (K/S computation for glycated hemoglobin), 7 pages.
Ignac et al., "Piddle Simple, personal, urine analysis," 2012, 5 pages.
Jung et al., "Rectangle Detection based on a Windowed Hough Transform," In Proceedings of the Computer Graphics and Image Processing, XVII Brazilian Symposium, IEEE Computer Society, 113-120, 2004.
Kerr, "Urine sample app lets users detect diseases with iPhones," Feb. 27, 2013, 2 pages.
Klein, "The Latest on Cellscope's Smartphone-Based Microscope and Otoscope," Jun. 21, 2012, 3 pages.
KurzweilAI—Accelerating Intelligence.News, "Students' cellphone screening device for anemia wins $250,000 prize," Jul. 26, 2012, 2 pages.
Lee, et al., "A Simple and Smart Telemedicine Device for Developing Regions: A Pocket-Sized Colorimetric Reader," Lab Chip. 2011, 11, 120, pp. 120-126, revised Jul. 19, 2010, 7 pages.
Medgadget, "Dario Smartphone Powered Glucose Monitor," Medicine, Net News, Pediatrics, Sep. 9, 2013, 3 pages.
Medgadget, "Medgadget Cell Phone-Based Imaging Technique to Read ELISA Results," Sep. 2011, 2 pages.
Microchip, Low-Power Linear Active ThermistorTM, 2009, 24 pages.
Mudanyali et al., "Integrated Rapid-Diagnostic-Test Reader Platform on a Cellphone," LAB on a Chip, vol. 12, No. 15, Apr. 16, 2012, 17 pages.
National Semi Conductor, "LPV7215 580 nA Rail-to-Rail Input and Output, 1.8V, Push-Pull Output Comparator," Sep. 2005, 7 pages.
Ostrovsky, "iBGstar Glucometer for iPhone Now Available in U.S.," May 4, 2012, 5 pages.
Ostrovsky, "iExaminer iPhone Adapter for Welch Allyn's PanOptic Ophthalmoscope Cleared in U.S. (w/video)," Jan. 24, 2013, 3 pages.
Ostrovsky, "Presentations from Health Hack Day Now available for Online Viewing," May 22, 2012, 4 pages.
PR Newswire, "Philosys Awarded CE Mark for new Gmate® SMART meter and seeks global telecommunications partners," Aug. 13, 2012, 2 pages.
PR Newswire, "Philosys Awarded CE Mark for New Gmate® SMART Meter an Seeks Global Telecommunications Partners," Aug. 13, 2012, 1 page.
PR Newswire, "Philosys, Inc. anticipates FDA Approval for New Gmate Blood Glucose Monitoring System," Aug. 2, 2012, 2 pages.
PR Newswire, "The New iPhone 5 and Gmate SMART Create a Dynamic Duo in Medical Diagnostics," Sep. 25, 2012, 2 pages.
Science Daily, "Hold the Phone for Vital Signs: Researchers Turn a Smart Phone into a Medical Monitor," Oct. 6, 2011, 3 pages.
Shen, et al., "Point-of-care colorimetric detection with a smartphone," Jul. 1, 2012, 4 pages.
Szeliski, "Computer Vision: Algorithms and Applications," Sep. 3, 2010, pp. 80-84 (Section 2.3.2).
Taos, "TCS3472 Color Light-To-Digital Converter with IR Filter," Texas Advanced Optoelectronic Solutions, Inc., Aug. 2012, 26 pages.
Texas Instruments, "100ppm/° C., 50 µA in SOT23-3 CMOS Voltage Reference," Jun. 2002, 16 pages.
Wakefield; "TED 2013, Uchek app tests urine for medical issues," BBC News Technology, Feb. 27, 2013, 4 pages.
Wang, et al., "Integration of cell phone imaging with microchip ELISA to detect ovarian cancer HE4 biomarker in urine at the point-of-care," Lab Chip, 11(20), pp. 3411-3418, Oct. 21, 2011, 16 pages.
Millipore, "Rapid Lateral Flow Test Strips," 2002, 42 pages.
Molecular Probes, "FluoSpheres Europium Luminescent Microspheres," Invitrogan, 2009, 3 pages.
You et al., "Household Fluorescent Lateral Flow Strip Platform for Sensitive and Quantitative Prognosis of Heart Failure Using Dual-Color Upconversion Nanoparticles," ACS Nano, May 8, 2017, 10 pages.
Pilavaki et al., "Optimized Lateral Flow Immunoassay Reader for the Detection of Infectious Diseases in Developing Countries," MDPI, Sensors, 2017, 11 pages.
Application and File History of U.S. Appl. No. 15/883,410, filed Jan. 30, 2018. Inventors Depa et al.
EP Application No. 21766977.9, Extended European Search Report dated Mar. 7, 2024, 8 pages.

* cited by examiner

DEVICES, SYSTEMS, AND METHODS FOR MEASURING BIOMARKERS IN BIOLOGICAL FLUIDS

RELATED APPLICATION

This application is a continuation of U.S. patent application Ser. No. 16/818,976 filed Mar. 13, 2020, now U.S. Pat. No. 11,536,732 issued Dec. 27, 2022, which is hereby fully incorporated herein by reference in its entirety.

FIELD OF TECHNOLOGY

Embodiments are related generally to measuring biomarkers in biological fluids, and more specifically to determining a concentration of creatinine in blood, plasma, or serum using a test strip and a portable optical sensing device paired to a mobile device.

BACKGROUND

Certain individuals require regular monitoring of analyte concentrations to aid in diagnosis and/or treatment of certain conditions such as, but not limited to, diabetes. For example, in diabetic monitoring applications, portable reader devices and corresponding test strip kits are commonly used by diabetic individuals or their physicians to detect high or low blood glucose levels. The monitored levels of glucose can aid in treatment and management of diabetes by notifying a user of abnormal levels, which allows the user to make necessary adjustments such as increasing sugar or insulin intake to stabilize blood glucose levels.

One such portable reader device for monitoring conditions, including diabetes, is commercially available as the Aina Device, available from the applicant of the present disclosure, which is described in U.S. Pat. No. 10,436,773 (application Ser. No. 14/997,749), entitled "Mobile Device Based Multi-Analyze Testing Analyzer for Use in Medical Diagnostic Monitoring and Screening," and at http://www.janacare.com/technology.html, all of which are incorporated herein by reference in their entireties. The portable reader device is connectable to a portable analyzer device, such as a smart phone, that has installed thereon algorithms for analyzing the reader device output, and quantifying the analyte concentration based on the reader device output.

Individuals may also or otherwise require regular monitoring of creatinine levels to ensure proper kidney and liver function. Creatinine levels are critically important in assessing renal function and muscle mass breakdown. Measurements of creatinine in serum or urine may also be used as indices in the diagnosis and treatment of other disorders such as muscular dystrophy and hypothyroidism. Thus, creatinine has been widely recognized as having vital medical significance. Although creatinine is primarily a waste product, and as such plays no important role in biochemical functions of the body, its chemical precursor, creatine, has a vital biochemical role. Creatine is a basic building block of creatine phosphate, which is the primary form of energy storage in muscle. As a result, the creatinine level is an important diagnostic index for renal, muscular, and thyroid function.

U.S. Pat. No. 3,907,644 to Mollering et al. (hereinafter "Mollering") discloses a method of converting creatinine into sarcosine and urea using creatinine amidohydrolase as the primary enzyme for creatinine measurement. Mollering discloses an assay performed in solution, focusing on creatine kinase as a coupling system for creatinine detection. However, Mollering and similar disclosures that would proceed via either creatine or ammonia were disfavored because each of those intermediates was present in the serum or urine sample being analyzed in varying, substantial concentrations compared to creatinine. To accurately determine the amount of creatinine in a sample, these methods require differential measurements on two separate or successive reaction mixtures, one in which first the free creatine or ammonia was determined and a second in which the portion of additional creatine or ammonia formed from creatinine was determined. The increased complexity and cost led researchers to focus on alternate enzymes permitting the reaction to proceed via pathways that would avoid either creatine or ammonia as intermediates.

These disclosures tend to focus on methods of stabilizing intermediate enzymes to improve the accuracy and precision of readings. For example, U.S. Pat. No. 4,645,739 to Deeg et al. (hereinafter "Deeg") describes a reaction pathway using N-methylhydantion and N-carbamylsarcosine as intermediates to avoid creatine and ammonia intermediates. Deeg discloses a method of determining the amount of creatinine present in a particular blood sample based on the amount of sarcosine that was present after conversion with these expensive and unstable enzymes. However, the pathway taught by Deeg relies on an expensive and unstable enzyme (1-methylhydantionase, or NMHase) that requires refrigeration. Thus, the test could not reasonably be performed outside a laboratory setting, and was subject to significant cost and performance limitations.

U.S. Pat. No. 5,374,546 to Nagel et al. (hereinafter "Nagel") describes an improvement upon the pathway disclosed in Deeg. Specifically, Nagel teaches that NMHase was stabilized by its own substrate, causing a blank reaction which could lead to wide variance in the final test results and inevitably required separate determination of the blank reaction for accurate measurements of creatinine levels. See Nagel, Col. 2, ll. 45-68. Additionally, Nagel points out that NMHase was unstable without its enzyme-bound substrate and could not be used for enzymatic methods such as creatinine determination. See Nagel, Col. 3, ll. 1-8. Thus, Nagel teaches a process of stabilizing NMHase, providing an improved and more exact method for the determination of creatinine or other analytes that could be detected via a reaction catalyzed by NMHase. However, Nagel's method continues to rely on the unstable NMHase as a catalyst and the required increased complexity of initially stabilizing the NMHase enzyme before ultimate performance of the desired enzymatic methods was possible.

U.S. Pat. App. No. 2006/0228767 to Shull et al. (hereinafter "Shull") teaches a method of measuring creatinine that avoided the costly and difficult procedure of stabilizing the NMHase bound to its substrate NMH. Shull discloses a method of using trinder reagents and test strip design features to achieve uniform flow in determining creatinine levels. Unlike prior test strips, Shull's test strip can measure a wide range of normal and pathological creatinine concentrations, without having to account for a blank reaction. See Shull at paragraphs [0021] and [0022]. The dry-chemistry creatinine test strip as disclosed in Shull is to be utilized as a cassette design having at least five distinct membranes, and Shull teaches that this design is vital to achieve accurate results because the added compressive force ensures precise and accurate readings. See, e.g., Shull, paragraph [0034]. However, Shull's design still incorporates an enzyme requiring stabilization, and continues to use a pathway that avoided having creatine or ammonia as intermediates, as previously described in the prior art. Additionally, the cassette and relatively large number of membranes required for the Shull test strip increase both cost and complexity.

U.S. RE41,264E to Cai et al. (hereinafter "Cai") details a method for improved creatinine detection. The method disclosed in Cai focuses on correcting for endogenous creatine interference through the use of an interference-correcting electrode. However, this design is still subject to measurement error, and the additional interference-correcting electrode increases the overall cost of diagnostic tools capable of performing the Cai method.

Thus there remains a need for a novel dry-chemistry creatinine test using a pathway with superior performance and simplicity, and preferably for use with a portable reader device, as described above.

SUMMARY

Embodiments are directed to platforms for enzymatic assays for biomarkers, including systems, methods, and measuring devices by which a biomarker, such as, but not limited to, creatinine, can be measured easily using a small amount of biological fluid, such as blood, plasma, or serum. The measuring device or biosensor according to embodiments comprises a test strip including a layered active component assembly sandwiched between two outer layers. The active component assembly enables multi-step enzymatic reactions operating in kinetic and/or endpoint (in which the reaction is allowed to near completion), and generally includes multiple layers with primary enzyme(s), coupling enzyme(s), and reagents to produce an optical signal correlated to the concentration of a biomarker in the sample, without the need for stabilizing enzymes, additional liquid handling steps by the end-user, and in the case of creatinine, without the need of background subtraction of endogenous creatine, or complexities associated with carefully controlling lag time to enable kinetic read out for creatine mitigation.

In embodiments, the chemistry of the test strip uses commercially available enzymes to convert the biomarker, such as creatinine, into a chromophoric species that is directly proportional to the concentration of the biomarker in the biological fluid. The test strip can be read using an optical sensing/reader device (or optoelectronic reader device) couplable to or containing an analyzer device with a central processing unit, such as a smart phone or tablet, for quickly detecting and measuring the biomarker concentration. The analyzer device can include an application or "app" which includes algorithms to quantify the concentration of the biomarker, such as creatinine, and correct for variable kinetics. For example, the test strip can be used in combination with the Aina Device, described above, coupled to a smart phone, tablet, or other portable computing device for monitoring a target biomarker concentration.

In certain embodiments, the test strip generally includes a top layer that can be either a backing card having structure defining an aperture for application of the sample, or a film, a sample application pad coupled to an inner-facing surface of the top layer, optional foam spacers placed on both sides of the application pad, an active interference mitigation layer (performing creatine removal in the case of a test for creatinine) positioned adjacent to or below the application pad and configured to enzymatically deplete an interfering species (such as creatine) in the sample, a detection layer in which a colorimetric response is induced by the presence of the biomarker (such as creatinine), an optional transient layer positioned between the mitigation layer and the detection layer to separate the depletion reaction (e.g. creatine depletion) and detection reaction in space and time, and a bottom layer that can be either a film coupled to the detection layer through which the optical readout is performed, or other layer, such as a backing card, having structure defining an aperture through which optical readout is performed. The top and bottom layers sandwich the active layers therebetween and to provide a barrier to prevent liquid from leaking out of the test strip during use.

The layers can be bonded together by any of a variety of bonding techniques, such as, for example, adhesives, heat sealable materials, or ultrasonic welding. In a particular embodiment, an optically clear adhesive layer is present between the detection layer and the bottom film layer so as not to interfere with optical signal detection. In an embodiment, the top and bottom film or backing card layers define the two outermost layers of the composite test strip, however, in alternative embodiments, additional layers and/or coatings can be incorporated as desired.

A kit and a method for using the kit for measuring a biomarker in a biological fluid to monitor a condition, according to embodiments, includes a plurality of test strips, and a set of instructions for preparing the test strip for measurement using an optical sensing device coupled to or incorporated into an analyzer device.

According to embodiments, a method for measuring the biomarker can include obtaining a fluid sample, such as a blood sample, applying the fluid sample to the application pad of the test strip, and inserting the test strip into an optical sensing device coupled to or incorporated into an analyzer device for measurement and analysis. In embodiments, the fluid sample can be applied before or after insertion of the test strip into the optical sensing device. The method can further include installing an application on a mobile device, pairing the mobile device with the optical sensing device, and collecting, reading, and/or analyzing the data in the application on the mobile device.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

The embodiments described below are not intended to be exhaustive or to limit the invention to the precise forms disclosed in the following detailed description. Rather the embodiments are chosen and described so that others skilled in the art may appreciate and understand the entire disclosure.

Referring to FIGS. 1A, 1B, 2A, and 2B, a biosensor device, or biosensor, comprises a composite test strip assembly 100 used for applying a sample and for inserting strip assembly 100 into an optical sensing device, such as an optoelectronic reader, either coupled to containing an analyzer device, for analysis of the sample. In embodiments, the sample is applied to test strip assembly 100 after insertion into the optical sensing device, while in other embodiments, the sample is applied to test strip assembly 100 before insertion into the optical sensing device.

In the embodiments depicted in FIGS. 1A, 1B, 2A and 2B, test strip assembly 100 comprises six layers. In alternative embodiments, more or less than six layers can be contemplated.

Test strip assembly 100 can comprise a top layer 102 that can be either a backing card having structure defining an aperture 112 (see FIGS. 1A and 1B), or a film (see FIGS. 2A and 2B), an optional spreading mesh application pad 104 coupled to top layer 102, one or more optional foam spacers 103 coupled to the top layer on each side of separation membrane 106 and detection layer 108 to provide support and structure to the test strip assembly 100, a functional separation membrane 106 positioned below application pad 104 and configured to mitigate interference, for instance from endogenous substances, and specifically endogenous creatine if the biomarker being measured is creatinine, in a blood or biological fluid sample, a detection layer 108, such as a treated membrane or substrate, positioned below separation membrane 106 and configured to induce a colorimetric response to the presence of the target biomarker, and a bottom layer 110 operably coupled to top layer 102 to sandwich components 103, 104, 106, and 108 here between and to provide optical access to the colorimetric response on detection layer 108.

Top layer 102 can be either a backing card or film formed from a plastic or polymeric material. Top layer 102 is also non-porous, and optionally hydrophobic, so as to not interfere with the fluid sample moving through the test strip assembly. Suitable backing card materials include, for example, polyethylene terephthalate (PET), vinyl materials, acetal copolymer, acrylic, nylon, polyester, polypropylene, polyphenylene sulfide, polyetheretherketone, poly(vinyl chloride), or combinations thereof. The preferred backing card contains a PET substrate coated with a high tack, high shear acrylic pressure sensitive adhesive. Suitable adhesive materials that are commercially available include, but are not limited to Lohmann GL-187, Kenosha KN-2211, FLEXcon H-529, and Dermamed DM-70001. Suitable film materials include, for example, polyethylene, polyvinyl chloride (PVC), polypropylene, polyethylene terephthalate (PET), polycarbonate, biaxially oriented polypropylene (BOPP), cyclic olefin copolymer, or combinations thereof.

Optional foam spacers 103 are formed from inert, non-wicking, hydrophobic foam material that provides spacing for the active layers 106, 108, and provides uniform pressure across the assembly 100. Spacers 103 allow for control of fluid transfer between and through the layers without the need of an external cassette (cartridge) or housing. The preferred spacer material is a conformable polyethylene foam. Alternative materials include, but are not limited to, polyurethane, polyester, vinyl, and cellulose coated with transfer adhesive. Suitable materials that are commercially available include FLEXcon dermaFLEX foam, 3M double sided polyethylene medical tape 1522, 3M spunlaced non-woven fabric 9917, and DermaMed non-woven tape.

Application pad 104, in the form of a spreading mesh, provides capillary force for directing flow of the fluid sample to membrane 106. The material is selected to reinforce membrane 106 and rapidly disburse the sample uniformly across a reaction zone of membrane 106, and can include, for example, a one-direction or multi-direction mesh or woven materials with consistent structure, thickness, and porosity. The material can optionally be treated with a hydrophilic treatment to provide sufficient spreading of the fluid sample. The fiber material can comprise, for example, nylon, fiberglass, a superabsorbent polymer such as a hydrogel, cellulose, or combinations thereof. In one embodiment, a monofilament yarn made of polyester or polyamide is selected, which has a large open area to minimize dead volume, such as in a range from about 10% to about 70%, and more particularly from about 43% to about 52%. One commercially available material for the spreading mesh is SAATICARE Hyphyl Polyester (285/44).

Separation membrane 106 can comprise a plasma separation membrane material or filter paper which can include an enzyme formulation and/or reagents (i.e. for elimination of potentially interfering substances, such as creatine in the case in which creatinine is the target biomarker). The substrate or filter paper is chosen to be compatible with the selected enzyme formulation, while minimizing lysis (i.e. rupturing of the blood cells) and dwell volume. Suitable materials that are commercially available include, for example, Pall Vivid Plasma Separation Membrane, Ahlstrom Cytosep HV or HV+, GE Fusion 5, and Ahlstrom 169.

According to the non-limiting embodiment in which creatinine is the target biomarker, the enzyme formulation can comprise a creatine eliminating enzyme such as creatine kinase or catalase. In some embodiments, the enzyme formulation is immobilized on particles which are embedded or otherwise deposited on or within membrane 106. Such particles can include, for example, latex, agarose, gold, silica, or combinations thereof. Immobilization by utilizing particles enhances the removal rate by driving the kinetics away from equilibrium as the fluid passes through the layer 106. In other embodiments, the enzyme formulation can be otherwise covalently coupled to membrane 106. In yet other embodiments, the enzyme is inactivated by selective precipitation or chelation of the enzyme and/or substrates using chelating agents or resins, alkaline earth metals, or titanium dioxide (TiO$_2$), or inhibitory reagents in the subsequent layer positioned below membrane 106.

Detection layer 108 comprises a treated membrane or paper layer chosen to produce color uniformly. The membrane or paper layer is treated with an enzyme formulation using commercially available enzymes. The formulation, such as when in the presence of creatinine when creatinine is the target biomarker (or other biomarker as contemplated in alternative embodiments), produces a colorimetric signal which is proportional to the concentration of the biomarker in the sample. More particularly, in an embodiment in which the target biomarker is creatinine, the enzyme formulation ultimately converts creatinine into hydrogen peroxide that is coupled with a chromogenic substrate to produce a colorimetric signal that is directly proportional to the concentration of creatinine in the sample. This process is mediated by the following enzymes: creatinine amidohydrolase, creatine amidinohydrolase, sarcosine oxidase, and peroxidase. Chromogenic reagents, i.e. Trinder pair, are utilized to generate the optical signal. The preferred Trinder pair, includes N-Ethyl-N-(2-hydroxy-3-sulfopropyl)-3,5-dimethylaniline (MAOS) and aminoantipyrine (4-AA), to generate the desired colorimetric response. Alternative chromogenic substrates, include, but are not limited to, N-Ethyl-N-(2-hydroxy-3-sulfopropyl)-3-methylaniline (TOOS), N-Ethyl-N-(3-sulfopropyl)aniline (ALPS), and Dojindo KN-dye. Using solution kinetic experiments, optimum assay conditions for minimizing assay time and costs were determined, and in embodiments, the reaction is carried out under a pH from 5.5 to 9.0 in a variety of Good's buffers, and more particularly, under a pH from 8.0 to 9.0 in N-Tris(hydroxymethyl)methyl-3-aminopropanesulfonic acid (TAPS) buffer.

In an embodiment, bottom layer 110 can be an optically clear film so that the colorimetric response in the reaction zone on treated substrate 108 can be detected by a reader. In this embodiment, any adhesive layer(s) (not shown) included to bond bottom film layer 110 to substrate 108 should also be optically clear. In an embodiment, bottom layer 110 can comprise a film or backing card which includes structure defining a readout window 114, such that the film or backing itself need not be optically clear. In other embodiments, the bottom layer is eliminated altogether. Suitable materials for the bottom layer 110 are the same as the suitable materials for the top layer 102 described above.

In embodiments, test strip assembly 100 is rectangular in shape, and has a length ranging from about 30 mm to about 80 mm so that it can be readily handled by the user. A thickness of top film layer 102 can range from about 0.1 mm to about 1 mm, so that when an aperture 112 is present in top film layer 102, a port is created for the application of a sample. More particularly, aperture 112 is formed into layer 102 by any of a variety of standard cutting techniques, such as, for example, die cutting or punching, laser cutting, or the like. Aperture 112 can be circular, as depicted, having a diameter ranging from about 2 to about 6 mm, allowing the reservoir to hold up a sample volume in a range from about 10 to about 50 µl. One of ordinary skill in the art would recognize that other aperture geometries can also be contemplated, including, for example, oval, square, rectangular, etc., with dimensions such that a similar sample volume can be contained. When aperture 112 is formed, certain structure of the sidewall may be desired for fast and smooth sample flow. For example, a sidewall of aperture 112 can be tapered, concave, convex, or substantially vertical.

In one particular embodiment, bottom layer 110 and/or top layer 102 comprise printed indicia thereon. The printed indicia can comprise any of a variety of text and/or graphics such as, for example, brand names, logos, arrows indicating the direction in which the test strip assembly 100 should be inserted into the optical sensing device for measurement, or any combination thereof.

In embodiments, test strip assembly 100 can be manufactured individually as discrete test strips. Alternatively, a plurality of test strip assemblies can be manufactured in roll form or in a card format, and upon assembly, individual test strip assemblies are converted or cut therefrom.

Figure 1A:
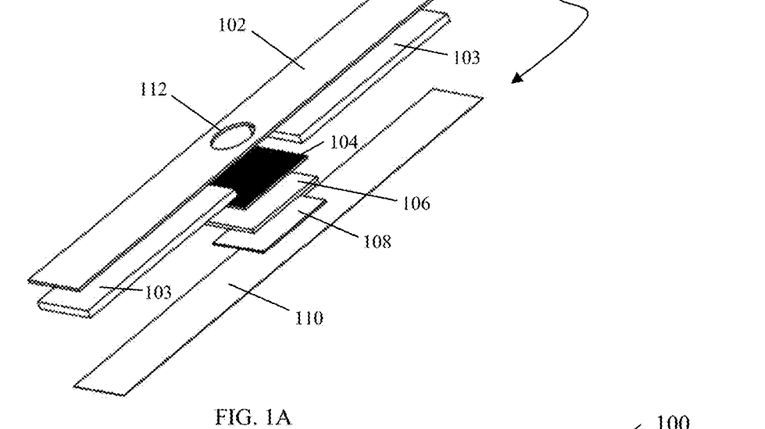
FIG. 1A is an exploded perspective view of a test strip assembly according to an embodiment.
Figure 1B:
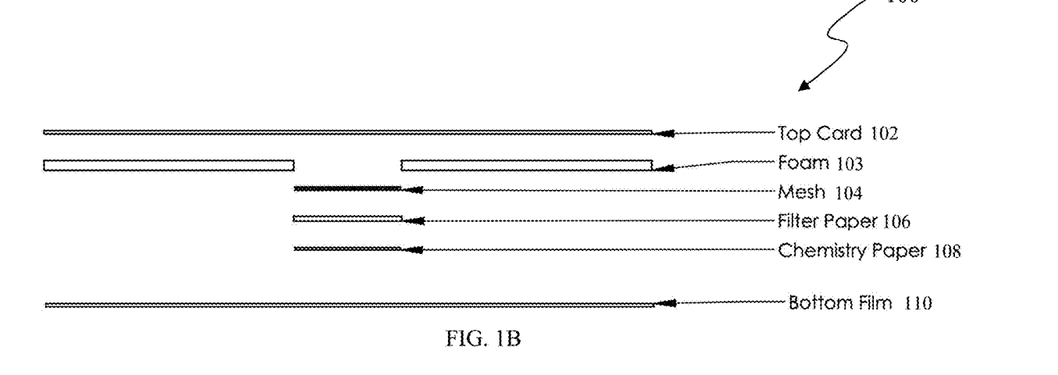
FIG. 1B is an exploded cross-sectional view of the test strip assembly of FIG. 1A.
Figure 2A:
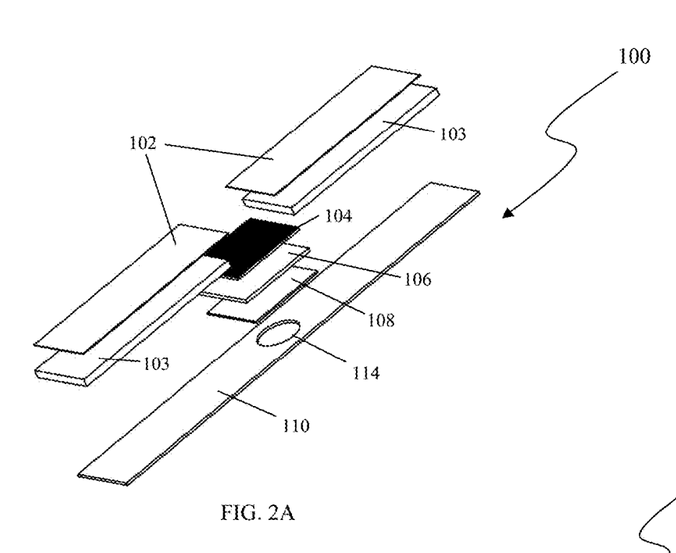
FIG. 2A is an exploded perspective view of a test strip assembly according to another embodiment.
Figure 2B:
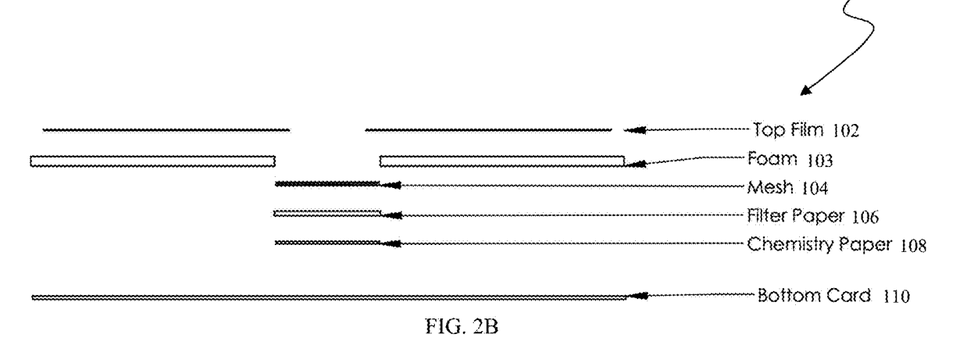
FIG. 2B is a cross-sectional view of the test strip assembly of FIG. 2A.
Figure 3A:
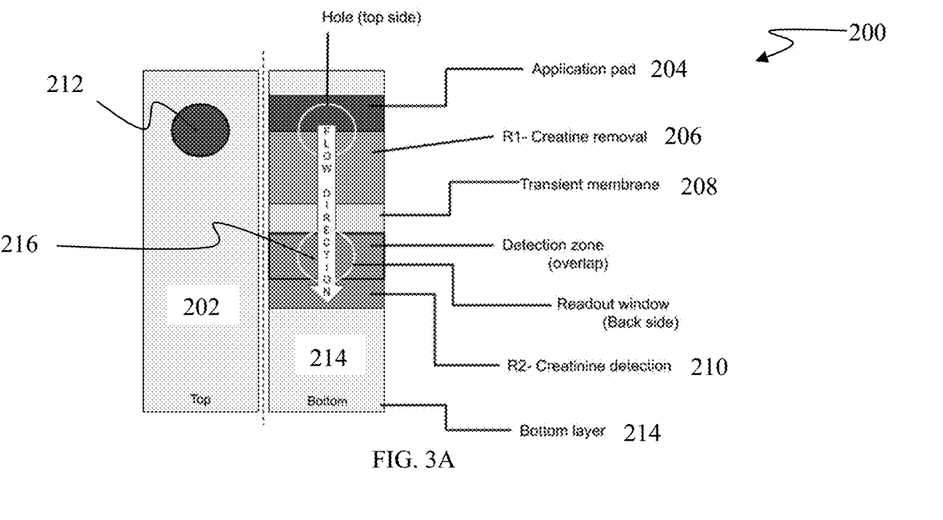
FIG. 3A is a top down view of a test strip assembly according to another embodiment.
Figure 3B:
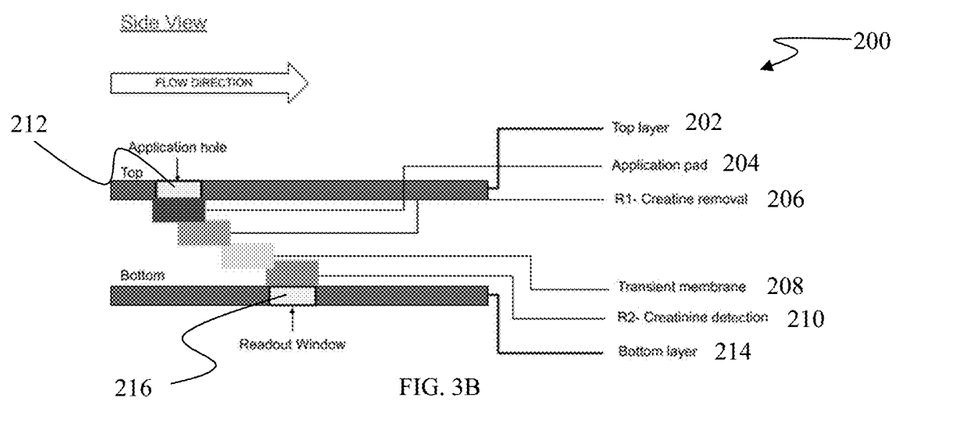
FIG. 3B is an exploded cross-sectional view of the test strip assembly of FIG. 3A.

Now referring to FIGS. 3A and 3B, in an alternative embodiment, a test strip assembly 200 utilizes a traditional wet chemistry of a two part reaction, but in a dry chemistry strip design to control timing and the flow of material through the strip to react out an otherwise interfering substance, such as endogenous creatine in the case in which creatinine is the target biomarker. Test strip assembly 200 is designed such that a mix of vertical and horizontal flow of the fluid sample allows for the transient and spatial separation of reagent components and allow for interfering substance, such as endogenous creatine, to be reacted out of the sample before the final reaction converts the target biomarker into a colorimetric signal. For sake of simplicity, test strip assembly 200 is described as for use in performing a creatinine assay; however, other biomarker assays can also be considered. Assembly 200 includes a top layer 202 as described above with respect to assembly 100, such as a backing card, with a sample aperture 212 formed in a first end of layer 202, an application pad 204 as described above with respect to assembly 100 positioned below aperture 212, a creatine removal or depletion reagent layer 206 positioned below and partially offset from application pad 204 along a longitudinal axis of assembly 200, an inert transient layer 208, such as a nylon layer, positioned below and partially offset from creatine removal layer 206 along the longitudinal axis of assembly 200, a creatinine detection layer 210 positioned below and partially offset from transient layer 208 along the longitudinal axis of assembly 200, and a bottom layer 214 coupled to the top layer 202 to sandwich components 204, 206, 208, and 210 therebetween.

Bottom layer 214 is similar to bottom layer 110 described above with respect to assembly 100. Bottom layer 214 can be formed of a polymeric film, such as a vinyl support, that is optionally optically clear, or can be formed of a film with structure defining a window 216 for optical access to detection layer 210. Window 216, if present, is longitudinally offset from aperture 212 along the longitudinal axis of assembly 200. The offset stacking of components 204, 206, 208, and 210 between the top and bottom film layers 202, 214 allow for both the vertical and horizontal flow of the fluid sample through test strip assembly 200.

Figure 6:
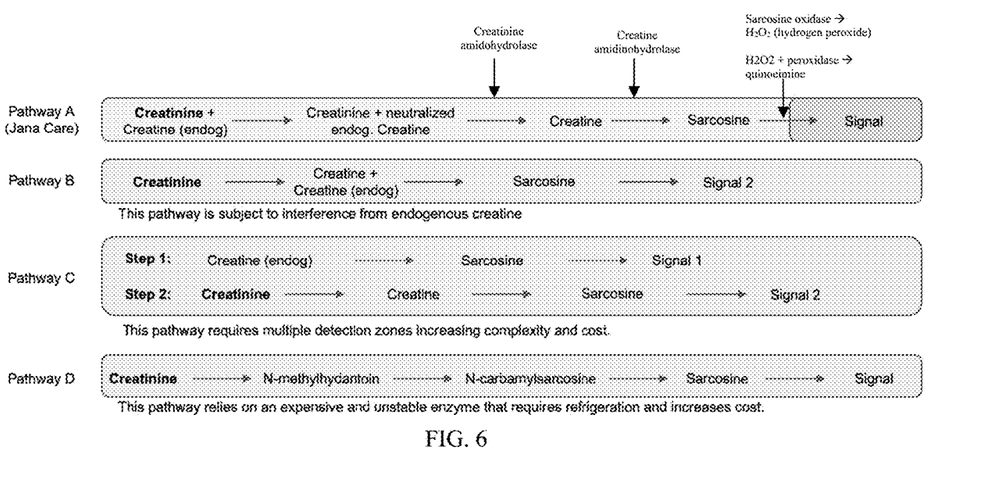
FIG. 6 depicts a flow chart of a creatinine test methodology according to an embodiment compared to methodologies of the prior art.

In this embodiment, both creatine removal layer 206 and creatinine detection layer 210 are formed of a treated nitrocellulose. As mentioned above, this embodiment incorporates a traditional wet chemistry scheme of a two-part reaction (on the creatine removal layer and the creatinine detection layer, respectively) with temporal separation via transient layer 208. For example, creatine removal layer 206 is treated with a creatine depletion reagent layer, that incorporates catalase in addition to the enzymes as described in layer 108, but excluding creatinine amidohydrolase, or creatine kinase, to react out endogenous creatine as the fluid sample moves through the strip. Creatinine detection layer 208 contains the full chemistry, as described for layer 108, to create a colorimetric response to the presence of biomarker in the sample. In one non-limiting example, and as depicted in FIG. 6 and labeled "Jana Care", the colorimetric response is created on creatinine detection layer by converting the creatinine to creatine and then to sacrosine, which is an amino acid produced by the hydrolysis of creatine, and which produces the signal. This example shows the simplicity of the assay compared to others as described in the Background section of the instant application.

Figure 4:
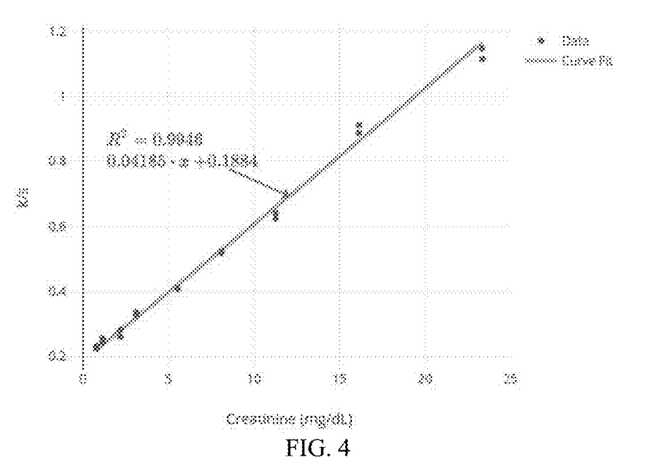
FIG. 4 is a graph demonstrating linear correlation of concentration of creatinine in blood and optical responses from various readings of test strips according to embodiments tested with whole blood samples and read on an optical reader.
Figure 5:
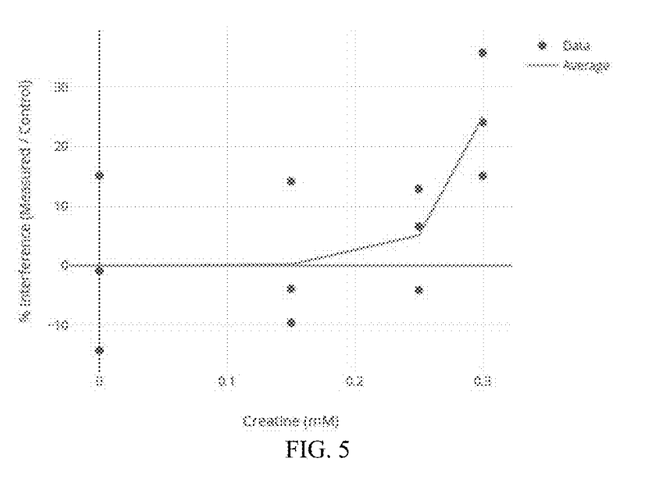
FIG. 5 is a graph demonstrating that test strips according to embodiments are not susceptible to significant interference from endogenous creatine levels below 0.25 mM.

In use, a biosensor comprising the test strip assembly according to embodiments is inserted into and read over time and at one or more wavelengths using an optical sensing device configured to be coupled to a measuring or analyzer device for analyzing a specimen, such as a blood sample, which will be described in more detail below. As depicted in FIG. 4, according to an embodiment, the optical signal measured in the reaction zone of a test strip can be used to take a measurement (such as reflection, absorbance, or k/s as per Kubelka-Munk theory) that is proportional to the concentration of the biomarker in whole blood. Specifically, the optical signal measurement is related to the concentration of creatinine in the sample, with an $R^2$ value close to 1. The relationship between the optical signal and biomarker concentration may be linear (i.e. direction proportional) or non-linear in nature. Further, referring now to FIG. 5, the creatinine assay described in the embodiments shows an average of less than 10% bias from nominal when less than 0.25 mM of creatine is present. More specifically, because endogenous creatine is removed from the sample before the creatinine is converted to a chromogenic species, the test strips are not susceptible to significant interference from endogenous creatine if present at levels below 0.3 mM. Keeping in mind that the normal range of creatine is between 0.013-0.097 mM in humans, the test design of the present embodiments is effectively impervious to creatine interference at physiological levels and renders a creatinine measurement directly without an additional measurement of endogenous creatine.

In an embodiment, the optical sensing device or reader is a photometer that comprises an optical block with a phototransducer, one or multiple light sources and an optional filter chosen to correspond to the chromophore, produced in the presence of the biomarker, i.e. the reaction on the detection layer of the test strip assemblies. The device, which will be described in more detail below, maximizes diffuse reflectance to capture measurements that are correlated with the concentration of the target analyte or biomarker. In an alternative embodiment, the optical sensing device is a spectrometer with light source(s) continuous over the spectral range of interest to provide full spectral imaging of the reaction.

A combination of two or more signals (i.e. wavelengths) may be used to allow for normalization of the signal to be done to compensate for slight variations in the background between different test strips and samples, and between different reader devices. Separation of the signals in time allows for variable enzyme activity in the test strip. The first or second derivative of the signals with respect to wavelength and/or time can be used to remove background noise, aid alignment of the signals in time, and detect when the reaction reaches completion.

Algorithms of the analyzer device include algorithms to quantify biomarkers and correct for variable kinetics. By measuring the strip before the reaction occurs and the final test strip at a specific endpoint at one or multiple wavelengths, variations in manufacturing and activity can be corrected to provide a more precise and accurate reading. Additionally, by measuring the signal over time, the reaction for the biomarker based on the endpoint can be separated out, instead of using a fixed readout time.

In a particular embodiment, the sensing device can comprise a hand-held reflectance based-optical sensor device. Once such suitable sensing device is commercially available as the Aina Device, available from the applicant of the present disclosure, and which is described in U.S. Pat. No. 10,436,773 (application Ser. No. 14/997,749), entitled "Mobile Device Based Multi-Analyze Testing Analyzer for Use in Medical Diagnostic Monitoring and Screening," and described at http://www.janacare.com/technology.html, all of which are incorporated herein by reference in their entireties. In embodiments, the sensing device connects to any of a variety of mobile devices, such as smartphones or tablets, through the audio jack or jack plug of the mobile device. Although generally referred to herein as "jack plug" for sake of convenience, a jack plug can include any wired or wireless communication element including, but not limited to, universal serial bus (USB), including micro USB and mini USB, Bluetooth®, near field communication (NFC), or WLAN (any IEEE 802.11 variant). The mobile device includes an application that runs on the mobile device for analyzing data generated by the device.

The device generally can include an adapter coupled to an optical sensing body containing optical or color sensing components within (internal, not shown, and as described, for example, in U.S. application Ser. No. 14/997,749). The adapter enables the detection layer or reaction area of the test strip assembly to align with the optical sensing components housed within the optical sensing body. The adapter includes structure defining a test strip insertion area, such as a slot or channel, for inserting test strips, such as test strip assembly described in the previous sections. When inserted, the test strip assembly is illuminated by one or several light sources, such as LED light sources, housed within the body. The light reflects from the detection layer of the test strip containing the biomarker converted to a chromophoric species, which is then measured by a light sensor, such as a photodiode. The reflected sensor value is then relayed to the mobile device where it is processed and analyzed by software algorithms contained in the application installed on the mobile device to produce a biomarker, such as creatinine, concentration reading. At each step, appropriate instructions are displayed on the mobile device's screen to guide the user in performing the test.

In an embodiment, the sensing device includes internal illumination light sources that allow for bright and consistent illumination, as described in U.S. patent application Ser. No. 14/997,749, incorporated by reference above. One such suitable source of illumination includes through-hole LEDs, which are cost-effective if high luminosity levels are required. To effectively measure the creatinine concentration on the test strip assembly described previously, the sensing device can comprise at least two separate illumination light sources at different wavelengths.

Optionally, in an embodiment, as the sensing device senses and transmits reflected color data to the mobile device for processing and analysis, the software on the mobile device performs various boundary checking to ensure that the test strip assembly is inserted properly at the different steps, and is not moved during the analysis. These algorithms may include, for example, simple checks such as checking if the reflected value is within a certain expected range, which can be performed simultaneously for the different wavelengths in which the test strip assembly is being analyzed.

As mentioned previously, the devices, systems, and methods according to embodiments provide a quick, portable, minimally invasive, and cost-efficient mechanism for measuring a biomarker, such as, but not limited to, creatinine, for monitoring or diagnosing a condition in a patient compared to those of the prior art. Unlike the devices and methods of the prior art, the devices, systems, and methods for determining the concentration of the biomarker, such as creatinine, according to embodiments utilize an efficient system to remove endogenous interfering substances such as creatine, enabling the use of enzymes not requiring additional stability, as well as without necessitating additional liquid handling steps by the end-user, background subtraction of endogenous substances such as creatine, complexities associated with carefully controlling lag time to enable kinetic read out for interfering substance or creatine mitigation, or proceeding through ammonia as an intermediate. Instead, embodiments enable the use of more stable enzymes and reduce measurement error by measuring the concentration of the biomarker (e.g. creatinine) directly without referencing the amount of interfering substance (e.g. creatine).

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A system for measuring a concentration of a biomarker in a sample of biological fluid using an optoelectronic reader coupled to a mobile device having a central processing unit, the system comprising:
    a biosensor including—
        a top layer;
        a bottom layer; and
        an active enzymatic component assembly positioned between the top and bottom layers, the assembly including—
            an interference mitigation layer positioned below the top layer, the interference mitigation layer being configured to receive the sample, and to enzymatically deplete or remove endogenous substance(s) therefrom, and
            a detection layer fluidly coupled to the interference mitigation layer to receive at least a portion of the sample therefrom, the detection layer being configured to enzymatically produce an optical response proportional to the concentration of the biomarker in the portion of the sample of the biological fluid, wherein the biosensor is configured to be positioned within an optoelectronic reader for detection of the optical response; and
    an optoelectronic reader configured to be coupled to the mobile device, the optoelectronic reader including—
    structure defining an aperture configured to permit light to pass into and out of the optoelectronic reader at a defined viewing axis,
    structure defining a slot for operable insertion of the biosensor, the slot being configured to orient the biosensor to intersect the defined viewing axis,
    a microcontroller configured to control electronic components on a circuit within the optoelectronic reader and to operably communicate with the central processing unit of the mobile device,
    at least one light source configured to emit light at a wavelength in a range from about 400 nm to about 700 nm,
    an optical system configured to detect optical signals from the biosensor, and
    a power source disposed within the optoelectronic reader and operatively coupled with the microcontroller, the at least one light source, and the optical system,
    wherein the optoelectronic reader is configured to communicate signals representative of optical signals from the optical system to the central processing unit of the mobile device to be analyzed to provide an estimate of a concentration of the biomarker in the portion of the sample of the biological fluid in which endogenous substance(s) have been removed.

2. The system of claim 1, wherein the biosensor further comprises:
    a sample application layer positioned between the top layer and the interference mitigation layer, the sample application layer being configured to direct at least a portion of the sample of the biological fluid to the interference mitigation layer.

3. The system of claim 1, wherein the detection layer comprises a substrate treated with a chromogenic reagent including an indicator configured to produce the optical response.

4. The system of claim 3, wherein the detection layer further includes an enzymatic formulation configured to convert the biomarker in the sample of the biological fluid into a substrate that reacts with the chromogenic reagent to produce the optical response.

5. The system of claim 4, wherein the enzymatic formulation is configured to convert the biomarker into hydrogen peroxide, and the chromogenic reagent comprises a Trinder pair configured to react with hydrogen peroxide.

6. The system of claim 5, wherein the system is configured to measure a concentration of creatinine.

7. The system of claim 6, wherein the enzymatic formulation includes a primary enzyme comprising creatinine amidohydrolase, and coupling enzymes comprising creatine amidinohydrolase, sarcosine oxidase, and peroxidase.

8. The system of claim 7, wherein the Trinder pair comprises MAOS (N-Ethyl-N-(2-hydroxy-3-sulfopropyl)-3, 5-dimethylaniline) and 4-AA (aminoantipyrine).

9. The system of claim 1, wherein the interference mitigation layer includes an enzyme and/or reagent for elimination of the endogenous substance(s).

10. The system of claim 9, wherein the interference mitigation layer comprises a substrate or membrane, and the enzyme is immobilized on particles embedded or applied to the substrate or membrane.

11. The system of claim 10, wherein the particles comprise particles of latex, agarose, gold, silica, or combinations thereof.

12. The system of claim 9, wherein the system comprises chelating agents, chelating resins, alkaline earth metals, titanium dioxide, or combinations thereof configured to inactivate the enzyme and enzymatic substrates thereof by selective precipitation or chelation.

13. The system of claim 9, wherein the enzyme is creatine kinase, the interference mitigation layer is configured to remove creatine, and wherein the system is configured to measure a concentration of creatinine.

14. The system of claim 1, wherein the bottom layer is optically clear.

15. The system of claim 1, wherein both the interference mitigation layer and the detection layer each include a reaction zone comprising a dry phase enzymatic formulation.

16. The system of claim 1, wherein the at least one light source comprises an LED.

17. The system of claim 1, wherein the optoelectronic reader is couplable to the mobile device via an audio jack of the mobile device.

18. The system of claim 1, wherein the optoelectronic reader is couplable to the mobile device via a wireless connection.

19. The system of claim 1, wherein the system is configured to measure a concentration of creatinine, and wherein the biosensor is a solid state test strip assembly configured to enzymatically remove creatine from the sample, and to enzymatically convert creatinine to a substance that is reactive with a chromogenic reagent to produce the optical signal for detection by the optical system.

* * * * *